(12) United States Patent
Falkenhagen et al.

(10) Patent No.: US 9,320,845 B2
(45) Date of Patent: Apr. 26, 2016

(54) SORBENT FOR REMOVING PROTEIN-BOUND SUBSTANCES

(75) Inventors: Dieter Falkenhagen, Krems (AT); Jens Hartmann, Furth (AT); Viktoria Weber, Krems/Donau (AT)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 516 days.

(21) Appl. No.: 13/146,003

(22) PCT Filed: Jan. 20, 2010

(86) PCT No.: PCT/AT2010/000016
§ 371 (c)(1),
(2), (4) Date: Nov. 11, 2011

(87) PCT Pub. No.: WO2010/083544
PCT Pub. Date: Jul. 29, 2010

(65) Prior Publication Data
US 2012/0125857 A1 May 24, 2012

(30) Foreign Application Priority Data
Jan. 22, 2009 (AT) .................................. A 112/2009

(51) Int. Cl.
| | |
|---|---|
| A61M 1/36 | (2006.01) |
| B01D 15/08 | (2006.01) |
| B01J 20/22 | (2006.01) |
| B01J 20/26 | (2006.01) |
| B01J 20/285 | (2006.01) |
| B01J 20/32 | (2006.01) |
| B01D 15/00 | (2006.01) |
| B01J 20/28 | (2006.01) |

(52) U.S. Cl.
CPC .............. *A61M 1/3679* (2013.01); *B01D 15/00* (2013.01); *B01D 15/08* (2013.01); *B01J 20/264* (2013.01); *B01J 20/265* (2013.01); *B01J 20/28004* (2013.01); *B01J 20/285* (2013.01); *B01J 20/28083* (2013.01); *B01J 20/321* (2013.01); *B01J 20/3253* (2013.01); *B01J 20/3255* (2013.01); *B01J 20/3274* (2013.01); *B01J 20/28023* (2013.01); *B01J 20/28085* (2013.01); *B01J 2220/58* (2013.01)

(58) Field of Classification Search
CPC ................. A61M 1/3679; B01J 20/267; B01J 20/28004; B01J 20/28078; B01J 20/328; B01J 20/28085; B01J 20/28023; B01J 20/321; B01J 20/3255; B01J 20/3253; B01J 2220/58; B01J 20/28083; B01J 20/264; B01J 20/265; B01J 20/285; B01J 20/3274; G01N 1/405; B01D 15/00; B01D 15/08
USPC .......... 210/638, 660, 690, 483, 488, 489, 490, 210/502.1, 504, 506; 436/528, 531, 86, 88; 604/4.01, 5.04; 502/7, 401, 402
See application file for complete search history.

(56) References Cited

U.S. PATENT DOCUMENTS

| | | | |
|---|---|---|---|
| 4,202,775 A * | 5/1980 | Abe et al. ...................... | 210/287 |
| 5,855,782 A | 1/1999 | Falkenhagen et al. | |
| 2007/0181499 A1 * | 8/2007 | Roberts et al. ................ | 210/645 |

FOREIGN PATENT DOCUMENTS

| | | |
|---|---|---|
| EP | 0776223 B1 | 6/1999 |
| WO | 2005082504 A2 | 9/2005 |

OTHER PUBLICATIONS

Annesini et al., "Bilirubin removal from albumin-containing solution by adsorption on polymer resin", The International Journal of Artificial Organs, vol. 28, No. 7, 2005, pp. 686-693.
Falkenhagen et al., "Optimization of albumin coating for resins", Artif. Organs, vol. 5, Jul. 1981, 2 pgs.
Falkenhagen et al., "The Prometheus-System", Technical Background and Clinical Experience, ASAIO 54th Annual Conference, Jun. 19-21, 2008, (Presented Lecture).
Hughes et al., "Albumin-Coated Amberlite XAD-7 Resin for Hemoperfusion in Acute Liver Failure, Part II: In Vivo Evaluation", HAS-Coated XAD-7, In Vivo Evaluation, Artificial Organs, vol. 3, No. 1, Feb. 1979, 4 pgs.
Hughes et al., "The use of an in vitro haemoperfusion circuit to evaluate the blood compatibility of albumin-coated Amberlite XAD-7 resin", The International Journal of Artificial Organs, vol. 1, No. 3, 1978, pp. 129-134.
Meijers et al., "Major Coagulation Disturbances During Fractionated Plasma Separation and Adsorption", American Journal of Transplantation 2007, 7: 2195-2199.
Ton et al., "Adsorption of Human Serum Albumin to Amberlite XAD-7 Resin", Journal of Biomedical Materials Research, vol. 13, 1979, pp. 407-422.
Ton et al., "Albumin-Coated Amberlite XAD-7 Resin for Hemoperfusion in Acute Liver Failure, Part I: Adsorption Studies", HSA-Coated XAD-7: Adsorption Studies, Artificial Organs, vol. 3, No. 1, Feb. 1979, 3 pgs.
Weber et al., "Neutral Styrene Divinylbenzene Copolymers for Adsorption of Toxins in Liver Failure", Biomacromolecules 2008, 9, pp. 1322-1328.

* cited by examiner

*Primary Examiner* — John Kim
(74) *Attorney, Agent, or Firm* — KPPB LLP (57) ABSTRACT

The invention relates to a sorption agent having improved selectivity properties for removing protein-bound substances from a biological fluid, in particular blood or blood plasma of patients having severe disturbances of the liver function or liver failure and having kidney insufficiency, thee sorption agent having: (a) a porous, neutral, hydrophobic polymer and (b) a polypeptide layer adsorbed on the polymer, the neutral, hydrophobic polymer having a mean pore size of at least 15 nm. Furthermore, the invention relates to methods and uses in connection with such a sorption agent. The invention is used in particular in extracorporeal liver support.

15 Claims, 7 Drawing Sheets

SORBENT FOR REMOVING PROTEIN-BOUND SUBSTANCES

The invention relates to a sorption agent for removing protein-bound substances from a biological fluid, the sorption agent having: (a) a porous, neutral hydrophobic polymer and (b) a polypeptide layer adsorbed on the polymer.

As the central metabolic organ, the liver has important tasks in glucose, protein, and fat metabolism, the storage of carbohydrates and vitamins, detoxification, and immune defense. Toxic substances and metabolic products which collect in the blood are removed from the blood by a functioning liver. In patients having reduced liver function or acute liver failure or liver failure induced because of a chronic illness, the blood must be freed of enriched toxic substances. Enrichment in the blood of liver toxins to be removed also occurs in persons having kidney insufficiency. Liver failure requires immediate hospital treatment, since the enrichment of toxic substances results in a short time in multiorgan complications up to the failure of various organs such as kidneys and lungs. A detoxification treatment is performed with the aid of an artificial liver support system ("artificial liver", liver dialysis), using which toxic substances can be effectively removed from the blood. Patients having life-threatening liver failure can thus be stabilized until the time of transplantation and kept alive. Since the liver has a high self-regeneration capability, a treatment which relieves the liver can even cause a resumption of the liver function of the patient. The effectiveness of the liver support system is decisive for the treatment success.

The toxic substances in the blood of patients with liver diseases can be divided into water-soluble and water-insoluble substances. Examples of toxic substances which are removed from the blood using a liver support system are unconjugated bilirubin, bile acids, predominantly aromatic amino acids, phenolic compounds, and ammonia. Water-insoluble liver toxins are in protein-bound form—typically to the blood protein albumin—for transport in the blood. Bilirubin is formed upon the degradation of hemoglobin and other hemoproteins (myoglobin, cytochrome). Since it is not water-soluble, it cannot be excreted via the kidneys. For transport in the blood, bilirubin is bound to albumin (unconjugated or indirect bilirubin). In the liver, bilirubin is coupled to glucuronic acid (conjugated or direct bilirubin). Conjugated bilirubin is water-soluble and can be excreted with the bile in the intestine or in the kidneys. In the event of failure of the liver function, conjugated bilirubin can no longer be formed and unconjugated bilirubin enriches in the blood. In the event of increased serum bilirubin level, jaundice then occurs, with yellow coloration of the sclera, the skin, and, in the event of a strongly elevated bilirubin level, also the tissue and organs. Bilirubin therefore represents an important marker for a disturbance or a failure of the liver function.

Extracorporeal liver support systems are known from the prior art. For removing protein-bound substances, extracorporeal liver support systems typically have a sorption apparatus (adsorber), which is situated in the extracorporeal blood circuit or in the plasma circuit and using which the protein-bound substances are eliminated from the blood or the plasma. The sorption apparatus contains a sorption agent (adsorbent). The efficiency of the sorption apparatus or the speed of the sorption (in particular adsorption) by the sorption agent is elementary for the treatment success or for the bridging stabilization of a patient, in particular a patient having liver failure.

The contact of blood or plasma with foreign surfaces results in contact activation and thereafter in coagulation, the release of kinins, and the activation of the complement system. These processes are also triggered by extracorporeal blood purification methods, since plasma or blood is brought into contact with membranes and adsorbers in the context of these methods. In most patients who require extracorporeal blood purification, an inhibition of the blood coagulation is therefore necessary. This is typically performed using heparin infusion. For patients for whom a heparin administration is contraindicated, regional anticoagulation can be performed using citrate.

Adsorbers based on an anion exchanger are very frequently used for clinical application in extracorporeal liver support systems. The liver dialysis device MARS (molecular adsorbent recircuit system) and the Prometheus system are to be mentioned as known devices in which anion exchangers are used for clinical application. Protein-bound toxic substances such as bilirubin can be removed very efficiently from a biological liquid such as blood plasma using an anion exchanger. In particular the Prometheus system is distinguished by a high clearance of protein bound and water-soluble liver toxins, whereby the survival rate of liver patients can be greatly increased. However, anion exchangers have the great disadvantage that not only the desired protein-bound substances, but rather also physiologically important proteins or factors of the blood coagulation system (anticoagulants and procoagulants) are eliminated to a very great extent. In particular coagulation inhibitors intrinsic to the patient, such as protein C and protein S, are to be mentioned here. Protein C is of particular importance as a coagulation-inhibiting factor. A reduction of the intracorporeal protein C concentration results in severe coagulation complications such as deep vein thromboses and lung embolisms. The anticoagulant heparin, which is additionally supplied via infusion into the extracorporeal blood circuit, is also eliminated by the anion exchanger. The result is an imbalance of the intracorporeal coagulation system or an undesired anticoagulation in the extracorporeal or intracorporeal blood circuit. This can be very problematic in particular for high-risk patients such as patients having liver failure and sepsis. A recent report deals with the great risk of occlusive thrombosis formation in the return of the extracorporeal blood purification system or in the patient after return of the purified blood due to the undesired binding proteins of the blood coagulation system on the anion exchanger [Meijers et al. 2007. Major Coagulation Disturbances During Fractionated Plasma Separation and Adsorption. Am J Transplant 7(9):2195-2199].

Because of the above-described disadvantages of an anion exchanger, the use of a neutral, hydrophobic polymer has been proposed. The polymer has pores in which the substances are adsorbed. The selected pore size of the polymer is a decisive factor. It has been shown in vitro that only pores larger than 5-6 nm are accessible to substances such as bilirubin, which are strongly bound to proteins. A good bilirubin adsorption has been established at a mean pore size of >7.5 nm [Weber et al. 2008. Neutral styrene divinylbenzene copolymers for adsorption of toxins in liver failure. Biomacromolecules 9(4):1322-1328]. The adsorption of protein-bound substances is better in the case of higher pore sizes because of the better pore accessibility. However, the capacity and thus the adsorption performance of the adsorber decreases again if an excessively large pore size is selected, since the internal surface area of the polymer decreases with increasing pore size.

Furthermore, it has been established for neutral, hydrophobic polymers that—in contrast to the above-described anion exchangers—only little heparin is bound. In addition, the formation of thrombin-antithrombin complexes is greatly reduced. However, it is disadvantageous that pronounced adsorption of protein C also occurs due to a neutral, hydrophobic polymer having a mean pore size >7.5 nm. It is to be assumed that other important proteins of similar molecular weight such as protein S, for example, are also adsorbed. Protein C would not be adsorbed with smaller pore sizes (<5-6 nm), which are inaccessible to strongly protein-bound substances.

Through the use of a neutral, hydrophobic polymer instead of an anion exchanger, an at least partially selective sorption agent could thus be provided, since the heparin adsorption could be greatly reduced or prevented. The adsorption of protein C by neutral, hydrophobic polymers is still so significant, however, that it can result in the above-described coagulation problems. This danger exists in particular in the case of patients for whom a heparin administration is contraindicated. The use of polymers of smaller pore size, in which protein C is not adsorbed, is not to be recommended, since the removal of protein-bound substances is inefficient. The adsorption efficiency for protein-bound substances is considered a decisive survival factor in the case of liver failure, as already emphasized.

A particularly high-performance system with respect to the removal of protein-bound substances is the Microspheres-based Detoxification System (MDS), which is known from EP 0776223 B1 and U.S. Pat. No. 5,855,782. A report was recently made about microsphere adsorber particles (mean particle size 5 μm) produced from a neutral, hydrophobic polymer (styrene/divinyl benzene copolymer, mean pore diameter: >100 nm) [Falkenhagen D., Vienken J., The Prometheus-System. Technical Background and Clinical Experience. ASAIO 54th Annual Conference, 19-21 Jun. 2008].

Furthermore, neutral resins for removing protein-bound substances are disclosed in WO 2005/082504 A2. WO 2005/082504 A2 describes a detoxification device, which has activated carbon and at least one non-ionic resin having a mean pore size of 30 nm (polystyrene divinyl benzene resin—Amberchrom GC 300C) or 45 nm (resin based on aliphatic esters Amberlite XAD-7HP). The above-described problems of neutral, hydrophobic polymers also apply to these neutral resin adsorbers.

A sorption agent and a method for producing a sorption agent of the type mentioned at the beginning were already disclosed at the end of the 1970s [Ton et al. 1979. Adsorption of Human Serum Albumin to Amberlite XAD-7 Resin. J Biomed Mater Res 13:407-422], [Hughes et al. 1978. The use of an in vitro haemoperfusion circuit to evaluate the blood compatibility of albumin-coated Amberlite XAD-7 resin. Int J Artif Organs 1(3):129-34], [Ton H. Y. et al. 1979. Albumin-coated Amberlite XAD-7 resin for hemoperfusion in acute liver failure. Part I: adsorption studies. Artif Organs 3(1):20-22], [Hughes R. et al. 1979. Albumin-coated Amberlite XAD-7 resin for hemoperfusion in acute liver failure. Part II: in vivo evaluation. Artif Organs. 3(1):23-26], [Falkenhagen et al. 1981. Optimization of albumin coating for resins. Artif Organs 5 (Suppl):195-199]. The adsorptive coating of neutral, hydrophobic resins such as Amberlite XAD-7 (mean pore size: 9 nm) or Y56 (mean pore size: 8 nm) using a polypeptide layer (albumin) has the goal of reducing the binding of thrombocytes to the adsorber and the thrombocyte loss connected thereto during a hemoperfusion.

In a further, more recent publication, which describes a sorption agent of the type mentioned at the beginning, it was reported that bilirubin is adsorbed better on an uncoated neutral resin (polystyrene divinyl benzene, pore size 5-10 nm) than on a neutral resin coated using an albumin layer [Annesini et al., 2005. Bilirubin removal from albumin-containing solution by adsorption on polymer resin. The International Journal of Artificial Organs. Vol 28, Nr. 7: 686-693]. The albumin layer adsorbed on the neutral resin therefore has a negative effect on the bilirubin adsorption and thus on the adsorption efficiency.

It is an object of the invention to provide an improved sorption agent. A sorption agent for removing protein-bound substances from a biological fluid having significantly improved selectivity properties in comparison to the sorption agent known from the prior art is to be provided. The improved sorption agent is to eliminate protein-bound substances in the blood of liver patients with high efficiency, while proteins which participate in blood coagulation, in particular important physiological coagulation-inhibiting factors such as protein C or protein S, remain in the biological fluid.

This object is achieved by a sorption agent of the type mentioned at the beginning, the neutral, hydrophobic polymer having a mean pore size of at least 15 nm.

Thanks to the invention, a sorption agent having significantly improved selectivity properties is provided, using which, on the one hand, a high-efficiency removal of protein-bound substances is ensured and, on the other hand, the coagulation problems, which are connected to neutral, hydrophobic polymers, can be avoided. The possibility is provided for the first time by the sorption agent according to the invention of, on the one hand, removing protein-bound substances efficiently from the blood of patients having severe disturbances of the liver function or liver failure and, on the other hand, reducing serious coagulation complications and thus improving the patient safety.

The inventors have established the surprising circumstance that the binding of protein C by the sorption agent according to the invention is significantly less in comparison to uncoated neutral, hydrophobic polymers if the mean pore size of the neutral, hydrophobic polymer before the coating with the polypeptide layer is at least 15 nm.

Protein C, a protein dependent on vitamin K in the blood plasma, is an important regulator of the blood coagulation sequence and has an anticoagulant effect. Undesired binding of protein C to uncoated neutral, hydrophobic polymers, as are known from the prior art, can therefore result in coagulation complications (deep vein thromboses, lung embolisms). It is to be assumed with great probability that the binding of protein S is also significantly reduced by the sorption agent according to the invention, as protein S (62,000 Da) has a similar relative molecular weight as protein C (69,000 Da). The same considerations apply for coagulation factors of similar molecular weight (e.g., factor VII, factor IX, and factor X).

In addition, it has been established that the sorption performance of the sorption agent according to the invention is impaired only insignificantly or not at all in relation to the protein-bound substances to be removed (e.g., bilirubin) in comparison to an uncoated polymer. The sorption agent according to the invention therefore also has an advantage in this point over the above-described sorption agent known from the prior art [see Annesini et al., 2005. Bilirubin removal from albumin-containing solution by adsorption on polymer resin. The International Journal of Artificial Organs. Vol 28, Nr. 7: 686-693].

Some of the terms used will be explained in greater detail hereafter for better understanding:

The term "sorption agent" in the context of this disclosure is an agent for performing a sorption, preferably an adsorption, i.e., molecules which are located in a biological fluid are fixed by the surface forces of the sorption agent. In the description, the terms "adsorption agent" or "adsorbent" or "adsorber" are also used instead of the term "sorption agent".

The expression "biological fluid" used in the scope of the invention can relate to cell-free liquids, in particular blood plasma, or to liquids containing cells, in particular blood. Since it is also necessary in the course of artificial liver support to introduce other liquids, for example, solutions containing coagulation inhibitors (heparin solution, citrate solution) or substitution solutions (electrolytes, liquids to compensate for the liquid loss) into the extracorporeal blood circuit or into a blood plasma circuit, a biological fluid is also to be understood as diluted blood or diluted blood plasma. The invention is primarily intended for the field of human medicine and therefore primarily relates to human biological fluids. However, this does not preclude the invention also being suitable for the field of veterinary medicine.

The expression "porous neutral, hydrophobic polymer" designates a porous, water-insoluble solid of defined mean pore size. It can be both a homopolymer and also a heteropolymer. The polymer has external and internal surfaces which are neutral and hydrophobic. The term "neutral" means non-ionic. The term "hydrophobic" is to be understood to mean that these are water-repellent material structures. Although a person skilled in the art in this field knows what the term "mean pore size of a polymer" is to be understood as and how the porosity or the mean pore size can be intentionally set, this term will nonetheless be briefly defined here for reasons of clarity. The mean pore size relates to the mean diameter of the pores. In the case of a Gaussian size distribution of the pore diameters, the mean pore diameter is the pore diameter which corresponds to the maximum of the distribution curve. The mean pore diameter can be determined using nitrogen adsorption [as described in Weber et al. 2008. Neutral styrene divinylbenzene copolymers for adsorption of toxins in liver failure. Biomacromolecules 9(4):1322-1328] or using mercury intrusion, for example. The pore size is set by variation of the concentration of the participating monomers, the solvent, or the modulator. The smaller the pores of the polymer are selected to be, the larger the internal surface area of the polymer which is available for sorption, in particular adsorption. The larger the pores, the better the accessibility of the pores for larger molecules. A production method of a polymer of defined pore size, as can be used for the invention, was described, e.g., by Weber et al. [Weber et al. 2008. Neutral styrene divinylbenzene copolymers for adsorption of toxins in liver failure. Biomacromolecules 9(4):1322-1328]. The invention is primarily oriented to particulate polymers. It would also be conceivable for the sorption agent to have the form of a membrane filter.

The external and internal surfaces of the porous, neutral, hydrophobic polymer are coated using a polypeptide layer, the polypeptide layer being formed by adsorption of polypeptide molecules on the surfaces of the polymer. The term "polypeptide" relates here to a polypeptide or a protein which is hydrophobic and has hydrophilic side chains or domains. The term polypeptide particularly relates to polypeptides which are synthesized from more than 10 amino acids, the number of the amino acids from which the polypeptide molecule is synthesized being open on top. In particular, the term polypeptide relates to proteins. During the adsorptive coating of the neutral, hydrophobic polymer using a polypeptide solution, the hydrophobic side chains or domains of the polypeptide (or protein) interact with the neutral, hydrophobic surface of the polymer because of the hydrophobic interaction. The hydrophobic interaction has great biochemical significance and is based on the phenomenon that hydrophobic molecules tend toward association in a polar environment. The hydrophobic interaction is therefore not a force per se, but rather is compelled by a polar environment. The hydrophilic side chains of the polypeptide are oriented outward, away from the hydrophobic surface of the polymer. The polymer is hydrophilized by lining its outer surfaces and its inner surfaces using the polypeptide layer. A polypeptide monolayer is typically formed. It is particularly expedient if the polypeptide layer is functionally inert, the term "functionally inert" being understood to mean that no specific interaction occurs between the polypeptide layer and the molecules (e.g., blood plasma proteins, etc.) present in the biological fluid. Furthermore, it is expedient if the polypeptide layer also does not interact non-specifically with the molecules present in the biological fluid. The suitability of a polypeptide for the present invention can be established by a person skilled in the art in the context of routine experiments.

It has been shown that protein C is removed from the biological fluid by a sorption agent according to the invention having a mean pore size of 15-20 nm after a certain time, namely when the biological fluid has been brought into contact for a sufficiently long time (longer than 15 minutes) with the sorption agent. In comparison to the sorption agent according to the invention, protein C is immediately eliminated by an uncoated neutral, hydrophobic polymer, however. A polymer having a mean pore size of 15-20 nm is nonetheless very well suitable for liver support systems having high adsorption speeds for strongly protein-bound substances, e.g., a Microspheres-based Detoxification System (MDS). The time in which the biological fluid is in contact with the sorption agent can be kept sufficiently short (less than 5 minutes) in MDS, so that physiologically relevant quantities of protein C still remain in the biological fluid. The advantage of a pore size of 15-20 nm is the larger internal surface area and the better sorption performance for protein-bound substances which accompany it.

In methods in which the biological fluid is in contact for a longer time (longer than 15 minutes) with the sorption agent according to the invention, it is recommended that a polymer having a mean pore size greater than 15-20 nm be used. It has been shown that the binding of protein C to the polymer is reduced further with increasing mean pore size. With higher pore sizes 30 nm), it is also possible to bring the biological fluid into contact with the sorption agent according to the invention for a very long period of time, without the protein C concentration decreasing to a physiologically critical value. With very high mean pore sizes of 80-100 nm, protein C is hardly still adsorbed. On the basis of this observation, the mean pore size of the neutral, hydrophobic polymer to be coated is to be selected as not less than 15 nm and preferably greater 30 nm). Protein-bound substances such as bilirubin are adsorbed very well at pore sizes of 15 nm or greater.

The use of albumin-coated polymers having small mean pore sizes of 8 or 9 nm (see the above-described prior art) does increase the biocompatibility with respect to reduced binding of the thrombocytes to the adsorber during hemoperfusion, but does not provide a satisfactory solution with respect to a reduction of the undesired protein C binding. The known albumin-coated polymers have not been connected up to this point to the coagulation problems with respect to protein C. In addition, as already noted in the prior art, a reduced bilirubin adsorption in comparison to the uncoated polymer has disadvantageously been established with albumin-coated polymers having a mean pore size of 5-10 nm.

One possible explanation for the decreasing protein C binding by the sorption agent with rising pore size could be as follows: The adsorptive coating of a polymer of small mean pore size (15-20 nm) using a polypeptide layer, in particular on the internal polymer surface, is possibly incomplete because of the size of the polypeptide used (e.g., albumin). The relatively small protein C can therefore slip into the pores and be adsorbed on the remaining hydrophobic surfaces. With higher mean pore sizes (>30 nm), better accessibility for the polypeptide and therefore also better hydrophilic lining of the polymer surface are provided. Therefore, hydrophobic surfaces would no longer be available for protein C. In addition, the protein C is repelled by the hydrophilic side chains or domains of the polypeptide layer. Since the sorption performance for protein-bound substances is not negatively influenced by the polypeptide coating, it is to be assumed that sufficient hydrophobic surfaces—which are not accessible to protein C, however—are still available on the internal surface for binding protein-bound substances on the coated polymer having greater pore size (>30 nm). The protein layer is presumed to form a monolayer, which has extremely small pores (picopores) between the individual polypeptide molecules, through which protein-bound substances such as bilirubin may pass and therefore can still be adsorbed in spite of the polypeptide coating.

Although the binding of protein C can be reduced to a minimum with a higher selected mean pore size of the uncoated polymer, it is favorable for the clinical application if the mean pore size is not greater than 80 nm. The internal surface area of the polymer would otherwise become too small. The result is a reduction of the sorption efficiency (adsorption efficiency) of strongly protein-bound substances. In high-risk patients having liver failure, it is recommended for the mean pore size to be selected as not greater than 40 nm.

In the case of a particularly preferred variant, the uncoated neutral, hydrophobic polymer has a mean pore size of 30 to 40 nm. It has been shown that in this variant, very little protein C is adsorbed, even if the biological fluid is brought into contact with the sorption agent over a long period of time. In addition, the internal surface area of the polymer is still large enough at this pore size that a high-efficiency adsorption of protein-bound substances is ensured.

Neutral, hydrophobic polymers, which have already been established in clinical practice, are advantageously used. A styrene/divinyl benzene copolymer is particularly preferably used. Styrene/divinyl benzene copolymers have proven themselves for the adsorption of toxins of liver and kidney failure and are distinguished by good biocompatibility, non-toxicity, and good stability and ability to be sterilized. In addition, the pore size can be set easily and reproducibly. Furthermore, very small particle sizes can be set. However, it is also possible to use neutral, hydrophobic polymers having a structure similar to a styrene/divinyl benzene copolymer; these should display a similar action as a styrene/divinyl benzene copolymer. It is possible for a person skilled in the art to establish in a few routine experiments whether a neutral, hydrophobic polymer is suitable for performing the invention.

Polypeptides having a relative molecular weight of 40,000 to 80,000 Da and/or a size dimension of up to approximately 10 nm×10 nm×10 nm are preferably used for coating the neutral, hydrophobic polymer with a polypeptide layer.

The polypeptide layer can comprise at least one type of polypeptide, the at least one type of polypeptide being selected from albumin, in particular human albumin, and albumin-like polypeptides. Albumin-like polypeptides are similar to albumin with respect to their structure and/or have albumin-like properties. Albumin-like polypeptides are recruited, inter alia, from subtypes of albumin, such as pre-albumin. The albumin-like polypeptides can either originate from natural sources or can be produced synthetically. The polypeptide layer can comprise a single type of polypeptide or a mixture of two or more types of polypeptide. The polypeptide can originate from a natural source and can also be produced recombinantly. The suitability of a polypeptide or a mixture of two or more types of polypeptide for the performance of the invention can be established by a person skilled in the art in the scope of routine experiments.

It will be noted once again here that the formation of the polypeptide layer on the internal and external surfaces of the neutral, hydrophobic polymer is based on a hydrophobic interaction between the hydrophobic side chains of the polypeptide or protein used and the hydrophobic surface of the polymer.

Because of the outstanding biocompatibility and the availability in high purity, the use of human albumin (human serum albumin, HSA) for coating the polymer is particularly favorable.

The invention further relates to a method for producing a sorption agent according to the invention, in which an up to 10% polypeptide solution is used for the adsorptive coating of the neutral, hydrophobic polymer with the polypeptide layer.

In a particularly preferred variant, the polypeptide solution is a human albumin solution. As already described in detail above, further advantageous polypeptides can be selected from albumin, in particular human albumin, and albumin-like polypeptides. In addition, the polypeptide solution can also contain more than one type of polypeptide.

It has been shown that a 1% polypeptide solution is already sufficient to provide a sorption agent with the properties according to the invention. The use of a more highly concentrated polypeptide solution (5-10%) does not result in significant differences or improvements with respect to the protein C binding. For economic reasons—high-purity polypeptide solutions are costly—in a first advantageous embodiment of the invention, a 1% polypeptide solution is therefore used for coating the neutral, hydrophobic polymer.

In a further advantageous embodiment of the method, a 10% polypeptide solution is used. The adsorptive coating of the polymer using a more highly concentrated polypeptide solution (10%) has the advantage that not only the undesired protein C binding to the sorption agent, but rather also the fibrinogen binding can be significantly reduced.

The pH value of the polypeptide solution is preferably set to 7.40. This has the advantage that a pH value which corresponds to the physiological pH value of blood is already used during the adsorptive coating of the carrier (polymer) with the polypeptide. This not only has advantages with respect to the patient safety (avoidance of acidosis or alkalosis), but rather also has advantages with respect to the production, since cumbersome washing procedures for setting a physiological pH value (the sorption agent is typically provided in the form of a suspension) are not necessary.

It can also prove to be favorable if the pH value is selected as close to the isoelectric point of the polypeptide. It is known that the occupation density of the polypeptide on the polymer is variable by varying the pH value [Ton et al. 1979. Adsorption of Human Serum Albumin to Amberlite XAD-7 Resin. J Biomed Mater Res 13:407-422]. The concentration of the polypeptide solution can be kept very low by optimizing the pH value, whereby production costs can be saved. The optimization of the pH value can be performed in the scope of routine experiments.

In addition to the physicochemical properties of the polymer surface and the mean pore size, the particle size of the polymer also plays a role in the adsorption procedure. The particle size influences the kinetics of the adsorption. The adsorption is essentially a function of the diffusion time (and therefore also the diffusion speed), which is in turn proportional to the square of the distance. With small selected particle sizes, the diffusion pathways are very short, whereby the speed of the elimination is inversely proportional to the particle size. In addition, with a small particle size, there is a large surface area/volume ratio. In order to make the sorption speed and the sorption capacity as great as possible for strongly protein-bound substances, it is advantageous if the sorption agent comprises microparticles, the microparticles having a particle size of 20 µm or less.

The microparticles are used in particular in MDS (Microspheres-based Detoxification System), which was already mentioned above in the prior art. The microparticles circulate as a suspension in a purification circuit (plasma circuit) on the filtrate side of a membrane filter. However, if the membrane filter becomes leaky, the danger exists that microparticles will reach the extracorporeal blood circuit and then the body of the patient and will result in a lung embolism therein. For this reason, it is provided in a particularly advantageous variant that the microparticles have a particle size of 8 µm or less, ideally 5 µm or less, since the danger of a lung embolism can be avoided at these small particle sizes.

Furthermore, the sorption agent according to the invention is a suitable filler material for a sorption apparatus, such as an adsorption column.

Furthermore, the invention relates to a method for removing protein-bound substances from a biological fluid, a biological fluid containing protein-bound substances being brought into contact with a sorption agent according to the invention. This can be performed above all in the scope of extracorporeal liver support, in which blood or blood plasma is purified of protein-bound substances using the sorption agent. Extracorporeal liver support is used in patients having liver failure or reduced liver function and in patients having kidney insufficiency. As described above, the biological fluid can pass a sorption apparatus which contains the sorption agent. However, the sorption agent can also be suspended in the biological fluid, as is used in an MDS.

Furthermore, the invention relates to the use of the sorption agent according to the invention as a selective sorption agent for removing protein-bound substances from a biological fluid, the protein-bound substances particularly being able to be bilirubin, aromatic amino acids, bile acids, phenols, and mercaptans. The term "protein-bound substances" primarily relates to protein-bound toxic materials (so-called liver toxins), which enrich in the blood in patients having liver functional disturbances or liver failure. The improved selectivity properties of the sorption agent according to the invention are based on a significant reduction with respect to the protein C binding by the sorption agent according to the invention, while the sorption performance for protein-bound substances is not impaired in comparison to the uncoated polymer.

The invention additionally relates to the use of the sorption agent according to the invention as a selective sorption agent for removing protein-bound substances from a cell-free biological fluid, in particular blood plasma.

Furthermore, the invention relates to the use of the sorption agent according to the invention as a selective sorption agent for removing protein-bound substances from a biological fluid containing cells, in particular blood.

The present invention will be explained in greater detail hereafter on the basis of nonrestrictive examples.

EXAMPLE 1

Production of Albumin-Coated Styrene/Divinyl Benzene Copolymers

The styrene-divinyl benzene copolymers of various mean pore sizes used for the coating are listed in Table 1, the particle size being 5 µm+/−3-4 µm:

TABLE 1

| styrene-divinyl benzene copolymers | |
|---|---|
| Designation of the styrene-divinyl benzene copolymer | Mean pore size (nm) |
| #1822 | 15-20 |
| #1824 | 30-40 |
| #1825 | 80-100 |

Firstly, a 50% suspension of a styrene/divinyl benzene copolymer of defined mean pore size is produced in physiological NaCl solution. Double the batch quantity thereof is pipetted into a 15 mL Greiner tube and centrifuged. The supernatant is withdrawn. The remaining styrene/divinyl benzene copolymer corresponds to the batch volume.

Subsequently, the styrene/divinyl benzene copolymer is coated using a human albumin layer by adsorbing human albumin from a human albumin solution on the external and internal surfaces of the copolymer. One tube having 1 mL copolymer and 5 mL human albumin solution (human serum albumin, HSA) (human albumin Octapharma 20% solution, Lot: B17B6331) is placed in each double batch. The concentration of the human albumin solution can be 1-10%. The tubes are incubated in the shaker (Enviro Genie®) at 10° C., frequency 25:50 for 21 hours. As a control, a tube having copolymer and 0.9% NaCl solution is carried along. A tube only having spiked plasma (see section 2.2.1) without copolymer is carried along as a negative control. After the end of the incubation time in the shaker (21 hours), the tubes are centrifuged and the supernatant is discarded.

EXAMPLE 2

Testing of Human-Albumin-Coated Styrene/Divinyl Benzene Copolymers of Various Pore Sizes with Respect to the Adsorption of Protein-Bound Substances and the Protein C Adsorption in Comparison to Uncoated Styrene/Divinyl Benzene Copolymers 2.1. Adsorbers Firstly, styrene/divinyl benzene copolymers of various pore sizes were provided. The particle size of the styrene/divinyl benzene copolymers was 5 µm+/−3-4 µm. The styrene/divinyl benzene copolymers were subsequently coated using a 10% human albumin solution (HSA) according to the production protocol from Example 1. The adsorbers are listed in Table 2:

TABLE 2

| Adsorbers (styrene/divinyl benzene copolymers) of various pore sizes with and without HSA coating | |
|---|---|
| ADSORBER DESIGNATION | Mean pore size (nm) |
| #1822 with HSA | 15-20 |
| #1822 without HSA | 15-20 |
| #1824 with HSA | 30-40 |
| #1824 without HSA | 30-40 |
| #1825 with HSA | 80-100 |
| #1825 without HSA | 80-100 |

The designation "with HSA" designates adsorbers which are coated using albumin, "without HSA" designates the respective uncoated adsorbers (=styrene/divinyl benzene copolymer without HSA coating).

2.2. Batch Test

The above listed adsorbers were studied in a batch test for their properties with respect to the adsorption of protein-bound substances and with respect to their protein C adsorption from human plasma. For these experiments, the adsorbers were coated using spiked plasma (see section 2.2.1.).

2.2.1. Production of a Plasma Spike:

For the production of a plasma spike, a plasma from a healthy donor was spiked using a defined concentration of liver toxins. 100 mL of spiked plasma contained liver toxins in the following concentrations: 300 µM bilirubin, 100 µM cholic acid, 100 µM tryptophan, 2 mM phenol.

The liver toxins were processed as follows:

For the bilirubin batch, 0.0175 g bilirubin was weighed and dissolved in 2 ml 0.3 N NaOH.

For the mixed toxin batch, 0.02043 g cholic acid, 0.0102 g tryptophan, and 0.0940 g phenol were weighed and stirred jointly into a total of 5 ml 0.3 N NaOH.

For 100 ml spiked plasma, 2 mL of the bilirubin batch and 1 mL of the mixed toxin batch were added to 96 mL plasma and stirred for 60 minutes slowly while protected from light. After 60 minutes, 3 mL 0.3 N HCl was added.

The adsorbers listed in Table 2 were coated in test tubes using spiked plasma, 1 mL adsorber being admixed with 9 mL spiked plasma. This corresponds to a 10% adsorber batch. As a negative control, a test tube having spiked plasma without adsorber was carried along. The test tubes were incubated for one hour at 37° C. on the Enviro Genie® shaker, frequency 25:50.

2.2.2. Sample Collection:

After 5, 15, 30, and 60 minutes, 1 mL was taken per test tube and immediately centrifuged for 10 minutes at 11,000 g. The supernatant was immediately transferred into an Eppendorf reaction vessel. The negative control without adsorber (designated as the "control plasma") was used for the measurement at the time 0 minutes. The samples were stored at −20° C., protected from light until the analysis.

2.2.3. Analysis:

Both the added liver toxins (bilirubin, cholic acid, tryptophan, phenol) and the adsorption of the proteins albumin and protein C present in the plasma were analyzed:
bilirubin, kit lot: 14652700 (Roche)
cholic acid, lot: R284067 (Roche)
tryptophan kit lot: 685125-01 (Roche)
phenol: HPLC chromatography
albumin kit lot: 688271-01 (Roche)
protein C ELISA kit lot: 12021228 (Technoclone)
The analysis was performed on a Hitachi 902 (VT).

2.3. Experimental Results:

Brief Description of the Drawings

The results of the experiments are shown in the figures in the form of graphs. In the figures.

2.4. Summary of the Results from the Batch Test:

The results of the batch test showed that the biocompatibility can be significantly improved by the albumin coating of the adsorber, in particular in that the adsorption of the natural anticoagulant protein C is prevented or greatly reduced. It is therefore to be presumed that this also applies for protein S. This is of great significance for patients having sepsis or liver failure, since the coagulation capability of the blood of these patients is disturbed and should not be additionally impaired. In addition, the characteristics of the adsorber with respect to the adsorption of essential toxins (see FIG. 1A, FIG. 1B, FIG. 2A, FIG. 2B, FIG. 3A, FIG. 3B, FIG. 4A, and FIG. 4B) of liver and kidney failure are not influenced by the HSA-protein coating, so that both their adsorption capacity and also their adsorption kinetics are largely maintained.

Figure 1A:
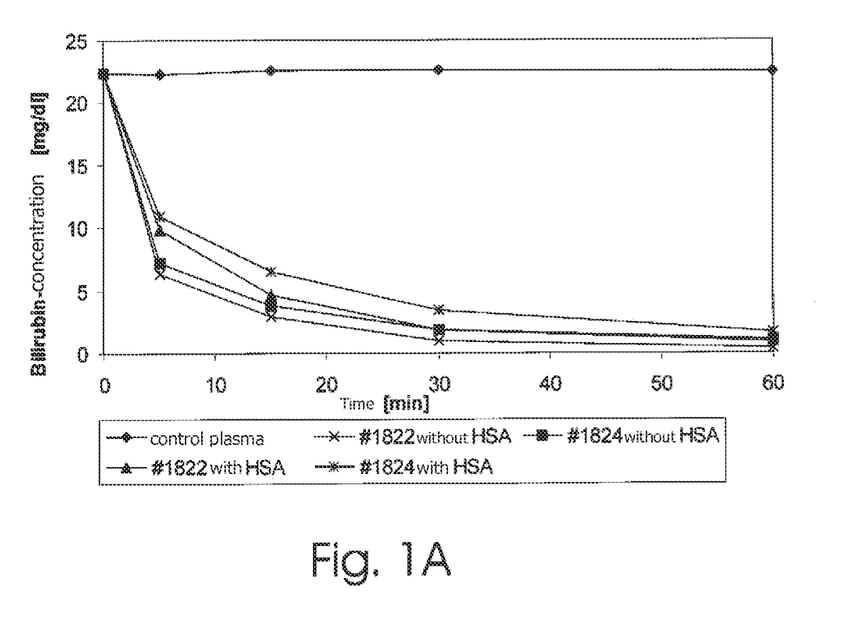
FIG. 1A shows the adsorption of bilirubin (bilirubin concentration in the supernatant in mg/dL) by the HSA-coated adsorbers #1822 with HSA and #1824 with HSA in comparison to the respective uncoated adsorbers #1822 without HSA and #1824 without HSA in the time curve [min]
Figure 1B:
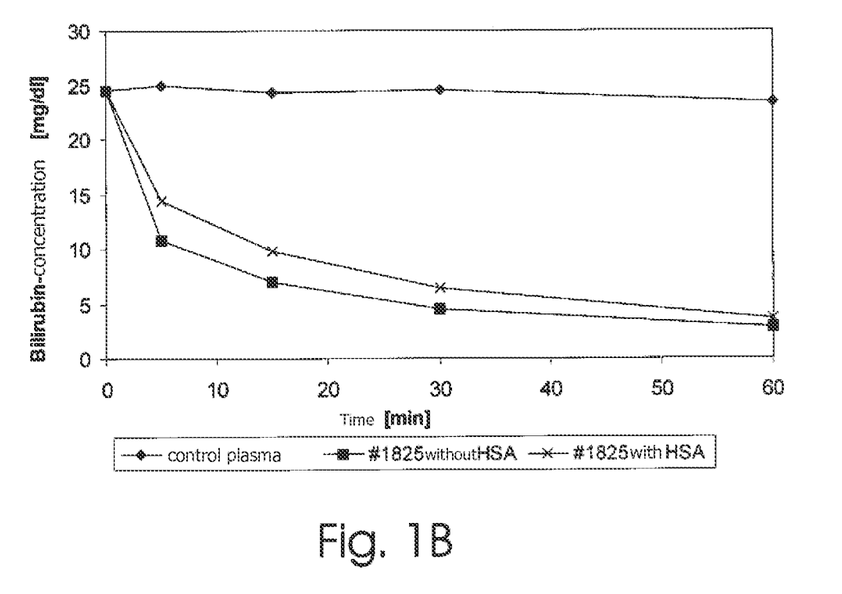
FIG. 1B shows the adsorption of bilirubin (bilirubin concentration in the supernatant in mg/dL) by the HSA-coated adsorbers #1825 with HSA in comparison to the uncoated adsorber #1825 without HSA in the time curve [min]
Figure 2A:
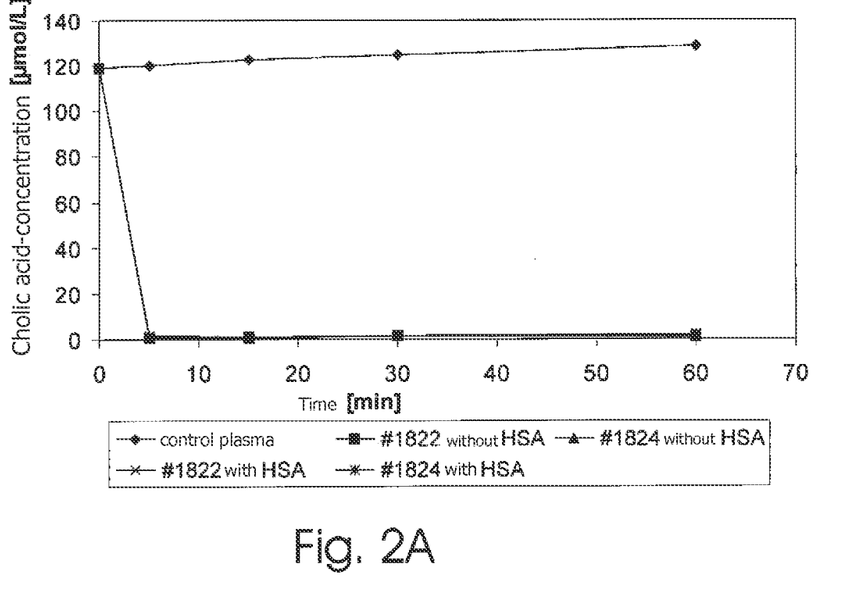
FIG. 2A shows the adsorption of cholic acid (cholic acid concentration in the supernatant in µmol/L) by the HSA-coated adsorbers #1822 with HSA and #1824 with HSA in comparison to the respective uncoated adsorbers #1822 without HSA and #1824 without HSA in the time curve [min]
Figure 2B:
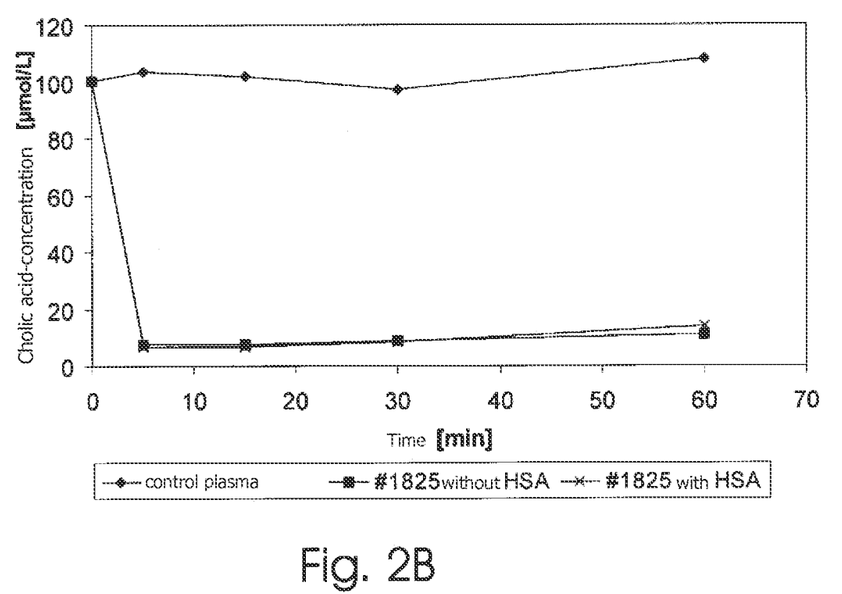
FIG. 2B shows the adsorption of cholic acid (cholic acid concentration in the supernatant in µmol/L) by the HSA-coated adsorbers #1825 with HSA in comparison to the uncoated adsorber #1825 without HSA in the time curve [min]
Figure 3A:
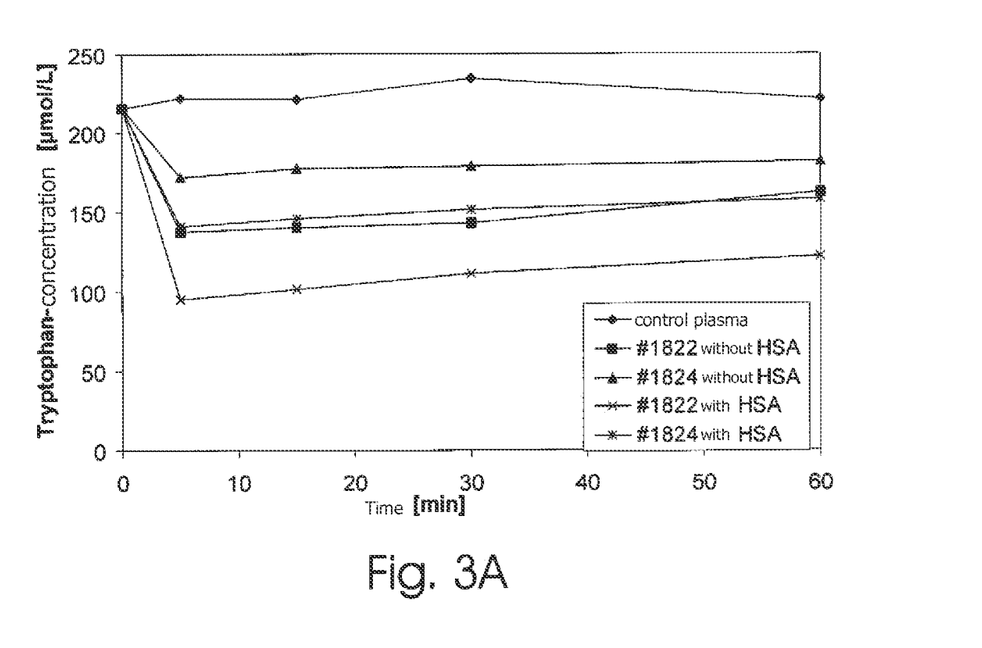
FIG. 3A shows the adsorption of tryptophan (tryptophan concentration in the supernatant in µmol/L) by the HSA-coated adsorbers #1822 with HSA and #1824 with HSA in comparison to the respective uncoated adsorbers #1822 without HSA and #1824 without HSA in the time curve [min]
Figure 3B:
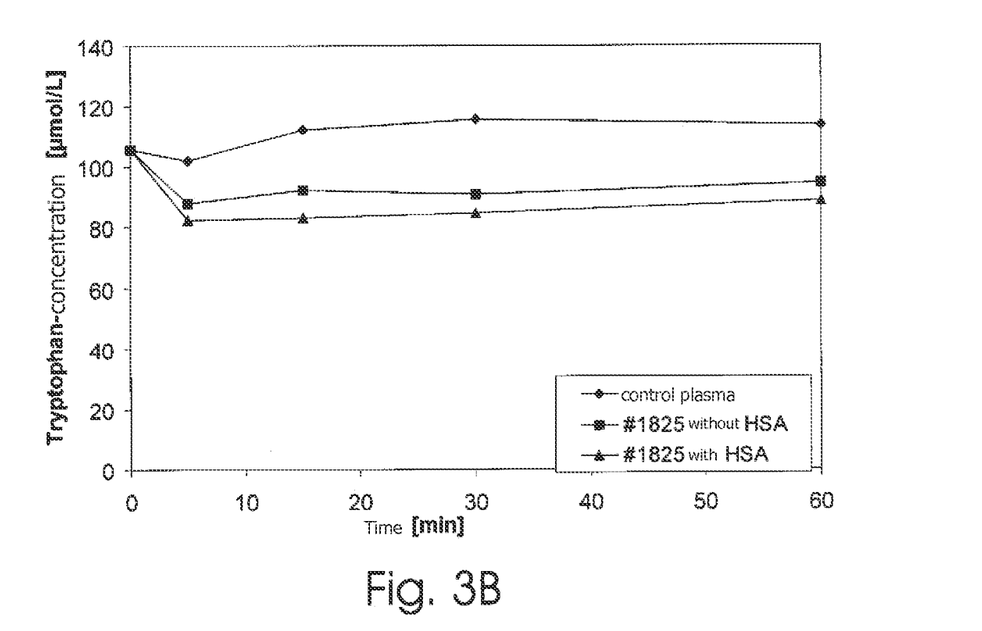
FIG. 3B shows the adsorption of tryptophan (tryptophan concentration in the supernatant in µmol/L) by the HSA-coated adsorbers #1825 with HSA in comparison to the uncoated adsorber #1825 without HSA in the time curve [min]
Figure 4A:
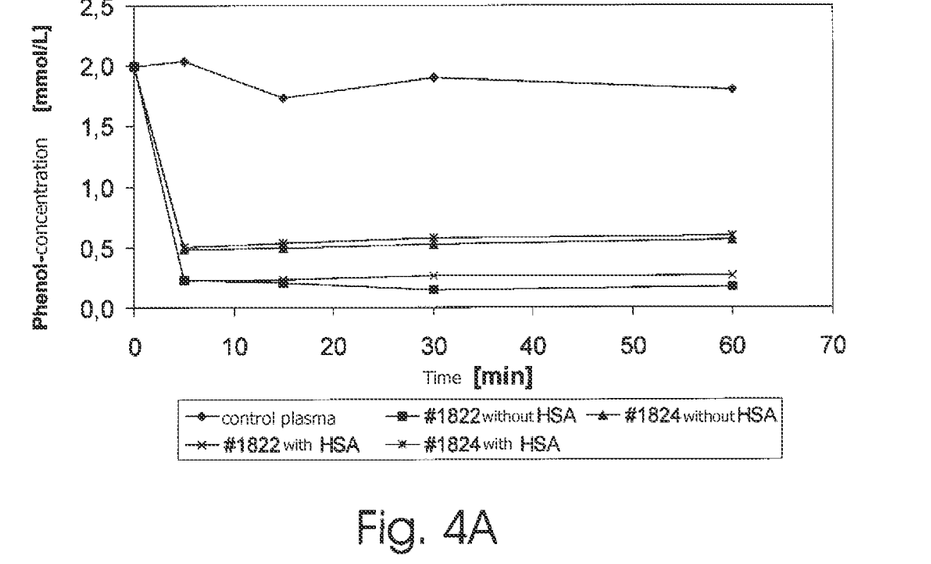
FIG. 4A shows the adsorption of phenol (phenol concentration in the supernatant in mmol/L) by the HSA-coated adsorbers #1822 with HSA and #1824 with HSA in comparison to the respective uncoated adsorbers #1822 without HSA and #1824 without HSA in the time curve [min]
Figure 4B:
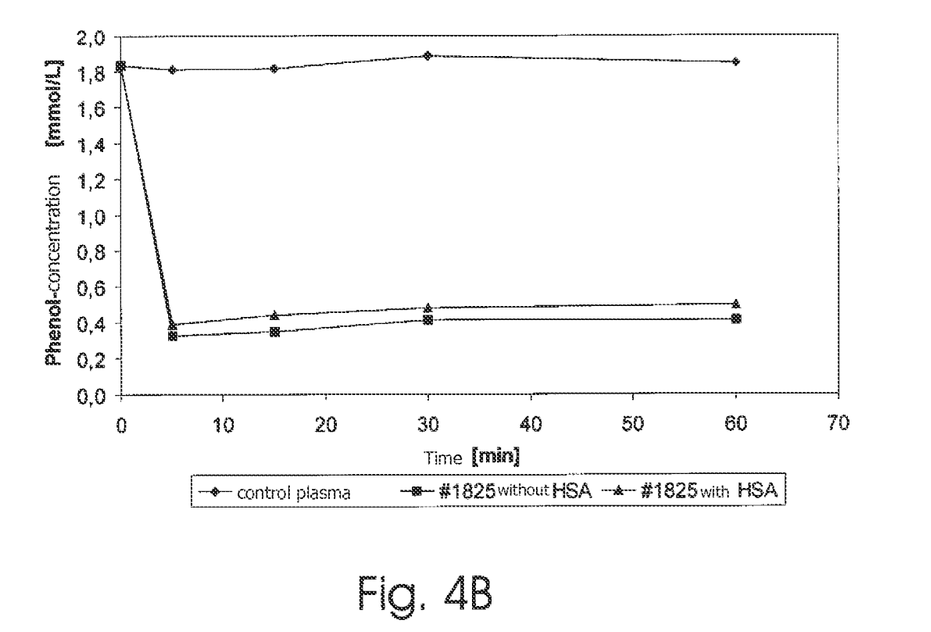
FIG. 4B shows the adsorption of phenol (phenol concentration in the supernatant in mmol/L) by the HSA-coated adsorbers #1825 with HSA in comparison to the uncoated adsorber #1825 without HSA in the time curve [min]
Figure 5A:
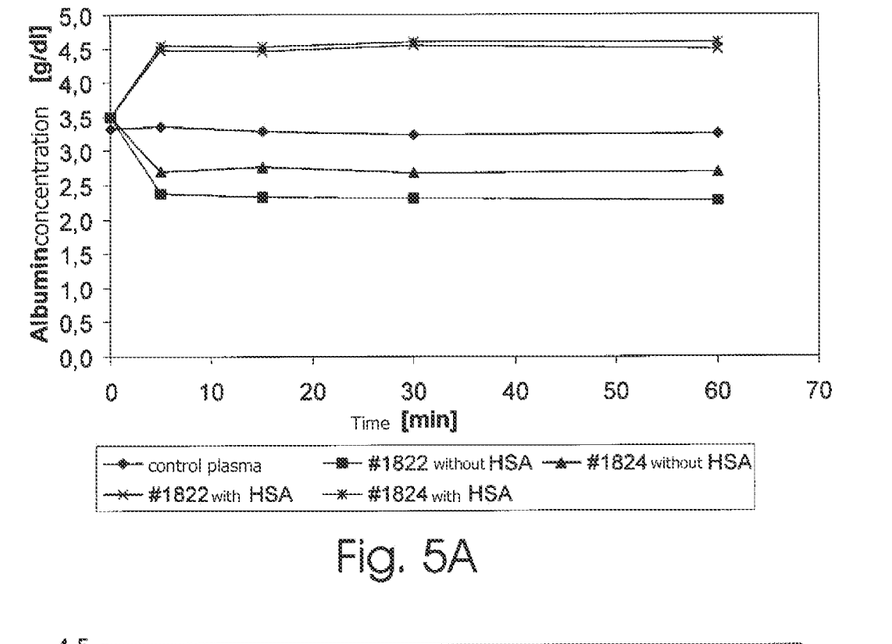
FIG. 5A shows the adsorption of the plasma protein albumin (albumin concentration in the supernatant in g/dL) by the HSA-coated adsorbers #1822 with HSA and #1824 with HSA in comparison to the respective uncoated adsorbers #1822 without HSA and #1824 without HSA in the time curve [min]
Figure 5B:
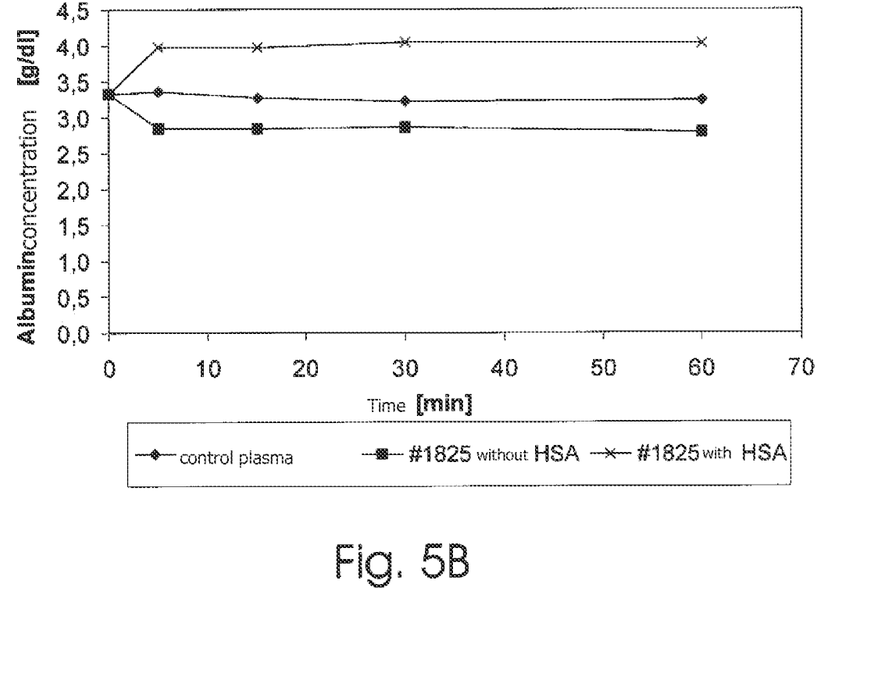
FIG. 5B shows the adsorption of the plasma protein albumin (albumin concentration in the supernatant in g/dL) by the HSA-coated adsorbers #1825 with HSA in comparison to the uncoated adsorber #1825 without HSA in the time curve [min]

The slight desorption of the albumin (see FIG. 5A and FIG. 5B) could be explained in that more albumin than needed binds to the polymer during the coating procedure and a double or multiple layer forms. The excess albumin is desorbed again under specific circumstances. The albumin monolayer, which is maintained in any case, is responsible for the described advantageous function of the albumin layer.

Figure 6:
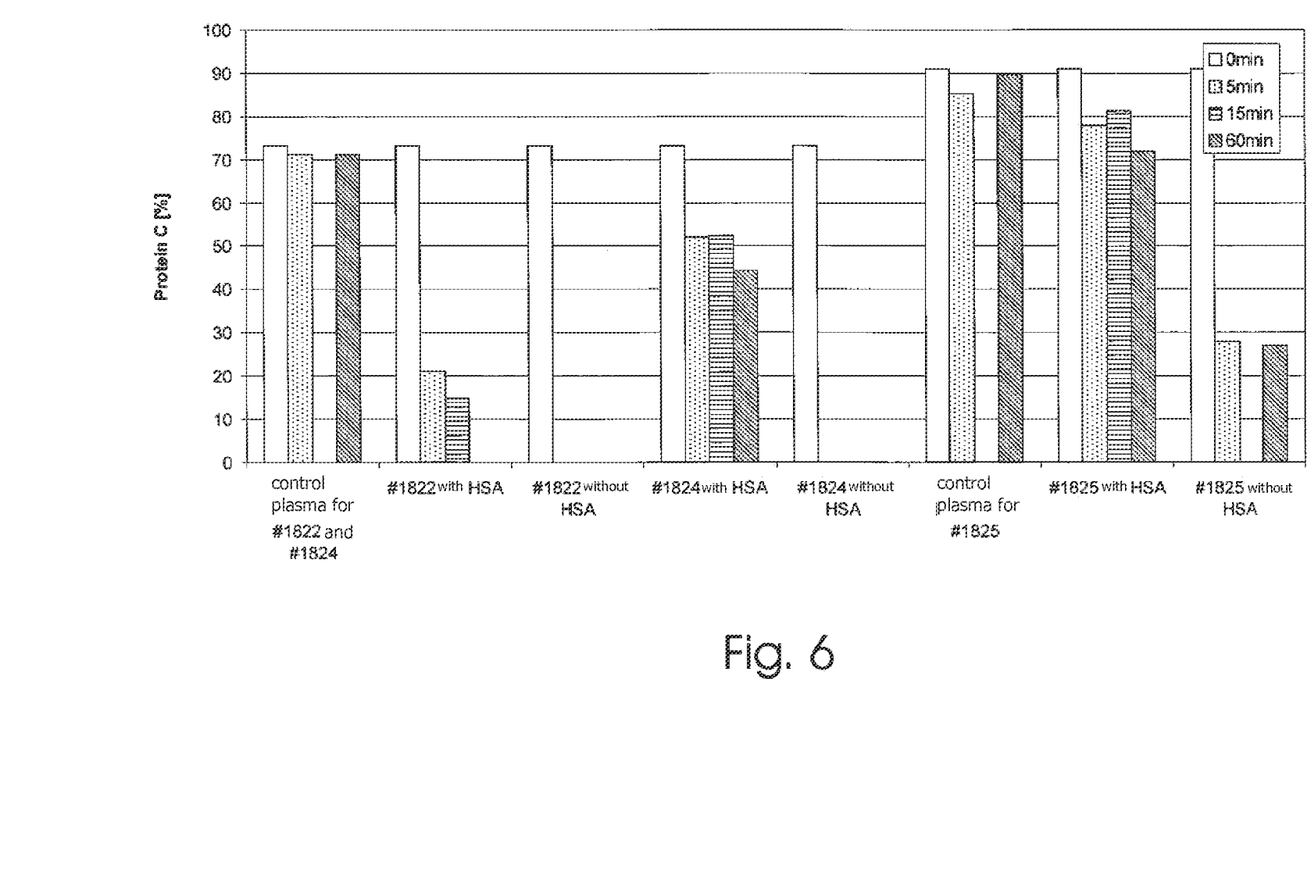
FIG. 6 shows the adsorption of the coagulation protein protein C (in %) by the HSA-coated adsorbers #1822 with HSA, #1824 with HSA and #1825 with HSA according to the invention in comparison to the respective uncoated adsorbers #1822 without HSA, #1824 without HSA, and #1825 without HSA after 0, 5, 15 and 60 min. incubation.

As can be clearly seen from FIG. 6, a significant reduction of the protein C adsorption can be achieved by the adsorptive coating of the styrene/divinyl benzene copolymer using a human albumin layer. While with the uncoated polymer having low mean pore sizes (15-20 nm and 30-40 nm), protein C is entirely eliminated from the plasma, with large mean pore sizes (#1825 without HSA, pore size 80-100 nm), a component of the protein C remains in the plasma. Adsorbers having pore sizes greater than 80 nm only have limited suitability for clinical application because of the reduced internal surface area, e.g., for patients having non-life-threatening liver function disturbances. In contrast to the uncoated adsorbers, a significant reduction of the protein C adsorption could already be established at a pore size of 15-20 nm using HSA-coated adsorbers. The protein C adsorption of the HSA-coated adsorbers decreases further with increasing pore size. It is particularly favorable if the HSA-coated adsorber has a pore size of 30-40 nm, since little protein C is eliminated at this pore size, on the one hand, and the internal surface area of the adsorber is still large enough for a high-efficiency removal of protein-bound substances, on the other hand. At high pore sizes (80-100 nm), protein C is hardly still adsorbed, however—as noted—the adsorption performance for protein-bound substances is also significantly less.

EXAMPLE 3

Testing Out the Adsorption of Protein-Bound Substances and Protein C as a Function of the Concentration of the Human Albumin Solution The influence of the concentration of a human albumin solution which is used for coating a neutral, hydrophobic styrene/divinyl copolymer (see protocol in Example 1), on the adsorption of protein-bound substances and protein C was tested. This experiment had the purpose of testing the ideal concentration of the human albumin solution for coating the copolymer.

The uncoated adsorber #1824 from Example 1 (mean pore size 30-40 nm) was coated using human albumin according to the protocol from Example 1, three different concentrations of the human albumin solution (1% HSA, 5% HSA, and 10% HSA) being used for the coating. In a batch test according to the protocol from section 2.2., the HSA-coated adsorbers were coated using spiked plasma. For comparison purposes, a tube having an uncoated adsorber was carried along. Furthermore, a tube only having spiked plasma without adsorber was carried along as a negative control. The analysis was also performed according to the protocol from section 2.2.

The various batches used in the batch test are listed in Table 3.

TABLE 3 batches for testing the concentration of the human albumin solution
negative control plasma

1824 without HSA
1824 1% HSA
1824 5% HSA
1824 10% HSA

Summary of the Results of the Batch Test:

The concentration of the HSA solution has no influence on the adsorption of bilirubin, cholic acid, albumin, and phenol. The curves are essentially congruent.

A slightly better tryptophan adsorption could be established at an HSA concentration of 10% than at HSA concentrations of 1% or 5%.

Figure 7:
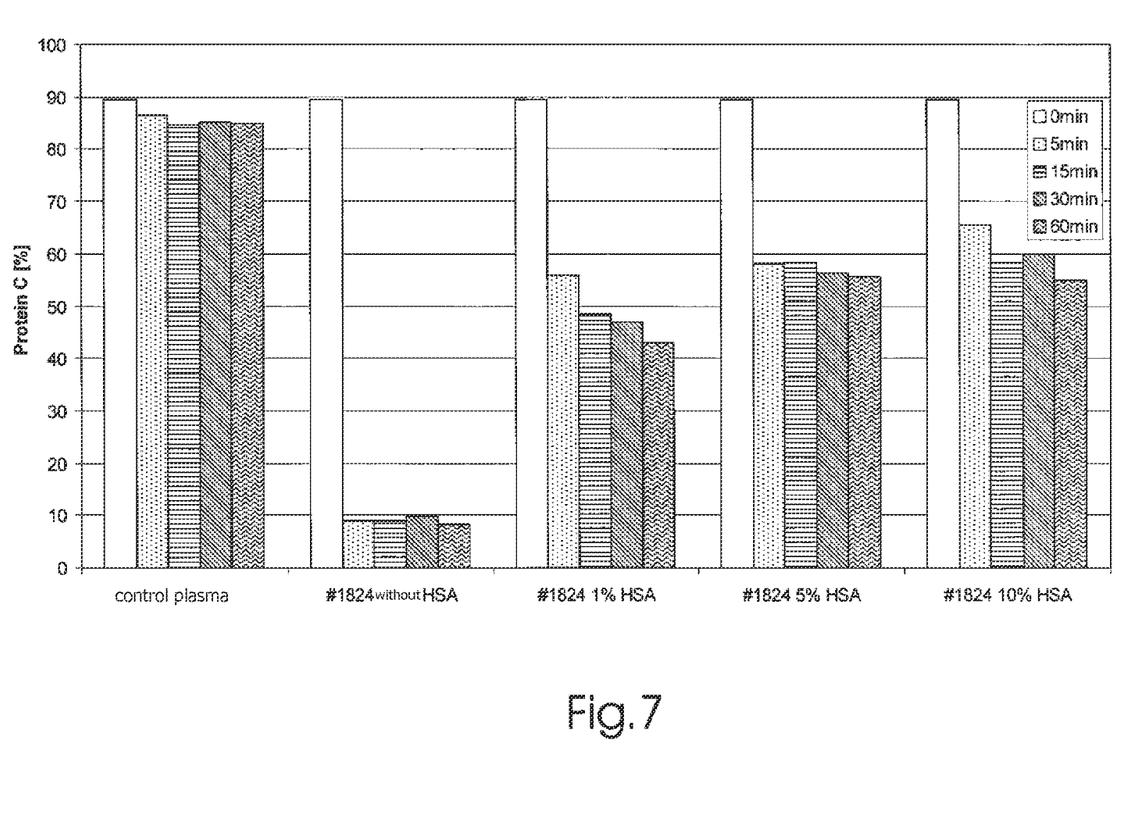
FIG. 7 shows the adsorption of the coagulation protein protein C (in %) by the adsorbers #1824 coated using various HSA solution of 1%, 5% and 10% as a function of time after 0, 5, 10, 30 and 60 min. incubation.

The adsorption of the coagulation protein protein C (in %) by the adsorbers coated using various human albumin solutions (1%, 5%, and 10%) is shown as a function of time (0, 5, 15, 30, and 60 minutes incubation) in FIG. 7.

The protein C adsorption is only insignificantly influenced by the concentration of the human albumin solution used for coating. Only a slight reduction of the protein C adsorption could be established upon rising concentration of the human albumin solution. On the basis of this result, a 1% human albumin solution for coating the polymer is entirely sufficient to greatly reduce adsorption of protein C.

Although a 1% human albumin solution is preferred for economic reasons, the use of a 10% human albumin solution for coating has advantages with respect to the adsorption of fibrinogen. While fibrinogen was completely eliminated from the plasma after a few minutes with 1% HSA and 5% HSA, the adsorption could be significantly reduced employing an adsorber coated using 10% HSA.

The invention claimed is:

1. A sorption agent for removing protein-bound substances from a biological fluid with reduced adsorption of Protein C, the sorption agent comprising:
  (a) a porous, neutral, hydrophobic polymer including microparticles, where the microparticles have a particle size of 20 μm or less and
  (b) a polypeptide layer adsorbed on the polymer,
  wherein the neutral, hydrophobic polymer is a styrene/divinyl benzene copolymer and has a mean pore size of 30-40 nm,
  wherein the polypeptide layer comprises at least one type of polypeptide selected from albumin, in particular human albumin, and albumin-like polypeptides, and
  wherein a 10% polypeptide solution is used for the adsorptive coating of the neutral, hydrophobic polymer with the polypeptide layer.

2. The sorption agent according to claim 1, wherein the microparticles have a particle size of 1 to 9 μm.

3. A sorption apparatus for removing protein-bound substances from a biological fluid with reduced adsorption of Protein C, containing a sorption agent comprising:
  (a) a porous, neutral, hydrophobic polymer including microparticles, where the microparticles have a particle size of 20 μm or less and
  (b) a polypeptide layer adsorbed on the polymer,
  wherein the neutral, hydrophobic polymer is a styrene/divinyl benzene copolymer and has a mean pore size of 30-40 nm,
  wherein the polypeptide layer comprises at least one type of polypeptide selected from albumin, in particular human albumin, and albumin-like polypeptides, and
  wherein a 10% polypeptide solution is used for the adsorptive coating of the neutral, hydrophobic polymer with the polypeptide layer.

4. The sorption apparatus according to claim 3, wherein the microparticles have a particle size of 1 to 9 μm.

5. A plasma circuit for removing protein-bound substances from a biological fluid with reduced adsorption of Protein C, containing a suspension of a sorption agent comprising:
  (a) a porous, neutral, hydrophobic polymer including microparticles, where the microparticles have a particle size of 20 μm or less and
  (b) a polypeptide layer adsorbed on the polymer, wherein the neutral, hydrophobic polymer is a styrene/divinyl benzene copolymer and has a mean pore size of 30-40 nm, wherein the polypeptide layer comprises at least one type of polypeptide selected from albumin, in particular human albumin, and albumin-like polypeptides, wherein a 10% polypeptide solution is used for the adsorptive coating of the neutral, hydrophobic polymer with the polypeptide layer.

6. The plasma circuit according to claim 5, wherein the microparticles have a particle size of 1 to 9 µm.

7. A method for producing a sorption agent comprising:

adsorptive coating a porous, neutral hydrophobic polymer with a polypeptide layer using a polypeptide solution, where the sorption agent comprises:

(a) the porous, neutral, hydrophobic polymer including microparticles, where the microparticles have a particle size of 20 µm or less and (b) the polypeptide layer is adsorbed on the polymer, wherein the neutral, hydrophobic polymer is a styrene/divinyl benzene copolymer and has a mean pore size of 30-40 nm, wherein the polypeptide layer comprises at least one type of polypeptide selected from albumin, in particular human albumin, and albumin-like polypeptides, and wherein the polypeptide solution is a 10% polypeptide solution.

8. The method according to claim 7, wherein the microparticles have a particle size of 1 to 9 µm.

9. A method for removing protein-bound substances from a biological fluid, comprising:

bringing a biological fluid containing protein-bound substances into contact with a sorption agent, where the sorption agent comprises:

(a) a porous, neutral, hydrophobic polymer including microparticles, where the microparticles have a particle size of 20 µm or less and (b) a polypeptide layer adsorbed on the polymer, wherein the neutral, hydrophobic polymer is a styrene/divinyl benzene copolymer and has a mean pore size of 30-40 nm, wherein the polypeptide layer comprises at least one type of polypeptide selected from albumin, in particular human albumin, and albumin-like polypeptides, and wherein a 10% polypeptide solution is used for an adsorptive coating of the neutral, hydrophobic polymer with the polypeptide layer.

10. The method according to claim 9, wherein the biological fluid is blood or blood plasma.

11. The method according to claim 9, where the protein-bound substances particularly being bilirubin, aromatic amino acids, bile acids, phenols, and mercaptans.

12. The method according to claim 9, wherein the selective sorption agent is used for removing protein-bound substances from blood plasma.

13. The method according to claim 9, wherein the selective sorption agent is used for removing protein-bound substances from blood.

14. The method according to claim 9, wherein the selective sorption agent is used in an MDS (Microsphere-based Detoxification System).

15. The method according to claim 9, wherein the microparticles have a particle size of 1 to 9 µm.

* * * * *